United States Patent [19]

Yamato et al.

[11] Patent Number: 4,501,737
[45] Date of Patent: Feb. 26, 1985

[54] PHARMACEUTICAL COMPOSITION CONTAINING 24,25-DIHYDROXYCHOLECALCIFEROL AS AN ACTIVE INGREDIENT TO TREAT MYODYSTROPHIA

[75] Inventors: Hideyuki Yamato, Tokyo; Noriyuki Toyoda, Sagamihara; Takayoshi Fujii, Tokyo; Yuji Maeda, Nagareyama; Tadaaki Kato, Tokyo; Chikao Yoshikumi, Kunitachi, all of Japan

[73] Assignee: Kureha Kagaku Kogyo Kabushiki Kaisha, Tokyo, Japan

[21] Appl. No.: 620,922

[22] Filed: Jun. 15, 1984

[30] Foreign Application Priority Data

Jun. 30, 1983 [JP] Japan .................................. 58-119427

[51] Int. Cl.$^3$ .............................................. A61K 31/59
[52] U.S. Cl. ................................................... 514/167
[58] Field of Search ........................................ 424/236

*Primary Examiner*—Stanley J. Friedman
*Attorney, Agent, or Firm*—Cushman, Darby & Cushman

[57] ABSTRACT

Disclosed is a pharmaceutical composition in dosage unit form which comprises a dosage effective for the treatment of myodystrophia of a compound of 24,25-dihydroxycholecalciferol and a pharmaceutical acceptable carrier or diluent therefor.

2 Claims, No Drawings

PHARMACEUTICAL COMPOSITION CONTAINING 24,25-DIHYDROXYCHOLECALCIFEROL AS AN ACTIVE INGREDIENT TO TREAT MYODYSTROPHIA

SUMMARY OF THE INVENTION

In a first aspect of the present invention, there is provided a pharmaceutical composition in dosage unit form which comprises a dosage effective for the treatment of myodystrophia of a compound of 24,25-dihydroxycholecalciferol and a pharmaceutical acceptable carrier or diluent therefor.

In a second aspect of the present invention, there is provided a method for the treatment of myodystrophia which comprises administering to a patient suffering from myodystrophia an effective amount of a compound of 24,25-dihydroxycholecalciferol.

DETAILED DESCRIPTION OF THE INVENTION

The present invention relates to a pharmaceutical composition containing 24,25-dihydroxycholecalciferol as an active ingredient for the treatment of myodystrophia.

As a result of the present inventors' studies on the endogenous substances present in healthy human body, of which the safety has been shown, it has been found that 24,25-dihydroxycholecalciferol (hereinafter referred to as 24,25-$(OH)_2$-$D_3$) has various physiological activities, and the present inventors have already found out the following activities in 24,25-$(OH)_2$-$D_3$.

Anti-hypercalcemic function, anti-ulcerous activity, preventive function from the reduction of immunofunction, regulative function of the metabolism of magnesium, anti-hyperphospheremic function, regulative function of blood sugar and anti-tumour function.

Subsequently, as a result of their continued studies on the physiological activity of 24,25-$(OH)_2$-$D_3$, the effectiveness thereof against myodystrophia was further found, and the present invention has been attained.

24,25-$(OH)_2$-$D_3$ is high in safety and acts effectively on myodystrophia and accordingly, is effective as an active ingredient of a pharmaceutical composition for the treatment of myodystrophia.

Myodystrophia is a myopathic syndrome characterized by the progressive degeneration of the skeletal muscles, and it is caused by some hereditary factors. Since an infantile case of pseudo hypertrophic-type myodistrophia has been precisely reported in 1868 by Duchenne, various clinical sub-type cases thereof were reported one after another. Accordingly, it has become understood that myodystrophia is a syndrome considerably rich in diversity.

In this connection, although a classification of myodystrophia has been carried out mainly from the clinical standpoint based on the age of onset of the disease, the distribution of the attacked muscles, the sexual difference in the patients, the hereditary types of the disease and the degree of acuteness of the progress of the disease, according to the classification carried out in 1968 by the World Neurological Union, myodystrophia can be broadly classified, as a hereditary disease, into (1) Duchenne (pseudohyperatrophic) type, (2) face-scapula-brachium type, (3) girdle type, (4) distal type, (5) ocular muscle type and (6) ocular-pharynx type. In addition, Walton and Gardner-Medwin classified both the Duchenne type and the girdle type according to the hereditary mode in 1969, and said that the name of the former should be limitedly used to those of the type of X-chromosome, and furthermore, they included myotonia in the classification of myodystrophia while classifying myotonia into the following three types, (i) congenital type, (ii) type aggravated by coldness and (iii) atrophic myotonic type.

The characteristic features of Duchenne type, as the representative example of myodystrophia, are as follows.

(A) Except for the very rare outbreak of Turner syndrome only on female, the outbreak of Duchenne type is observed only on male, thus suggesting sex-linked ressecive inheritance of the disease, (B) the outbreak thereof is observed on children of age of 2 to 5, (C) at first, the reduction of strength of the muscles of the pelvic arch appears followed by the symmetrical attack of the muscles, (D) pseudohypertrophy is necessarily observed mainly on the muscles of the lower thigh, (E) the symptoms are usually progressive and aggravating and the patient becomes unable to walk within 10 years after the onset, (F) disturbance of the heart muscles is frequently observed on the patient, (G) lordosis at the waist and scoliosis appear aggravatingly on the patient and (H) many of the patients attacked by myodystrophia die of mulnutrition, infectious respiratory disease and heart failure in their age of nearly 20.

Myodystrophia is one of the so-called refractory diseases and any treatment or drug which completely cure the disease has not been found yet and accordingly, the discovery of a treatment or a drug which is expected to prolongate the life of the patient of myodystrophia will be an important and large progress.

Every one of 24,25-$(OH)_2$-$D_3$ is a substance publicly known and represented by one of the following formulae, and is disclosed, for instance, in "Vitamin D; Molecular Biology and Clinical Nutrition" by Anthony W. Norman, pages 1 to 92 (1980).

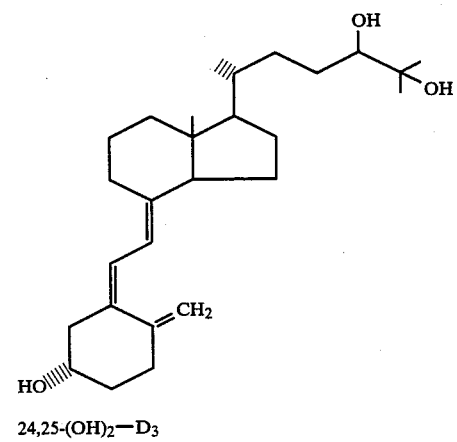

24,25-$(OH)_2$—$D_3$

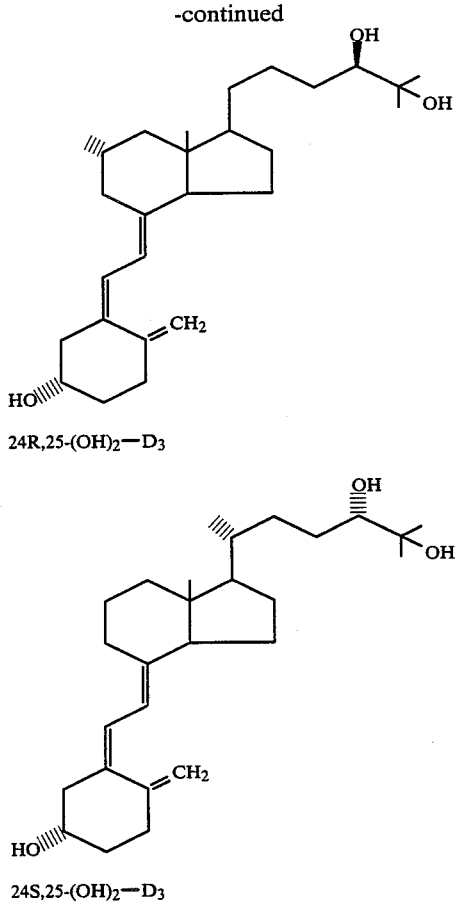

24R,25-(OH)$_2$—D$_3$ 24S,25-(OH)$_2$—D$_3$

Namely, 24,25-dihydroxycholecalciferol may be 24R,25-(OH)$_2$-D$_3$, 24S,25-(OH)$_2$-D$_3$ or a mixture thereof, however, in particular, it is preferably 24R,25-(OH)$_2$-D$_3$.

The pharmaceutical composition according to the present invention contains an effective amount of the above-mentioned substance as an active ingredient, and is used in dosage unit form with various types of formulation. The pharmaceutical composition can be administered orally or parenterally (including rectal route), the oral administration being preferable.

The pharmaceutical composition containing 24,25-(OH)$_2$-D$_3$ as an active ingredient is used as an administrative form such as tablet, powder, granule, suppository, encapsulation, solution in alcoholic medium or in oily medium and aqueous suspension. As the oily medium, triglycerides of C$_8$ to C$_{10}$ fatty acid, corn oil, cotton seed oil, peanut oil, fish-liver oil, cacao bean oil or glycerol is preferably used.

In addition, as the other component, lactose, starch, talc, magnesium stearate, sorbic acid, sorbate salts, sugars and sugar alcohols, physiological saline solution, surfactant, antioxidant or other medicine can be admixed with 24,25-(OH)$_2$-D$_3$.

The pharmaceutical composition according to the present invention may contain, in unit dosage form thereof, $2 \times 10^{-5}$ to 4% by weight, preferably $2 \times 10^{-4}$ to 1% by weight of 24,25-(OH)$_2$-D$_3$. 24,25-(OH)$_2$-D$_3$ is administered to an adult patient at a daily dose of 0.1 to $1 \times 10^5$ μg, preferably 0.5 to $1 \times 10^4$ μg.

The results of examination of the acute toxicity of 24,25-(OH)$_2$-D$_3$ are shown as follows.

An ethanolic solution of 24R,25-(OH)$_2$-D$_3$ or 24S,25-(OH)$_2$-D$_3$ was dissolved into triglyceride of C$_8$ to C$_{10}$ fatty acid to prepare a specimen containing 2% by weight of ethanol.

The thus prepared specimen was orally administered once to each of a group of ten male ICR-mice of body weight of 25±3 g at a dosage of 100 mg/kg body weight. Observation of the thus treated mice on their symptoms of intoxication for 2 weeks after the administration gave no abnormal findings on the mice without any death.

The results of examinations carried out after sacrificing each of the mice, including blood examination, biochemical examination, autopsy and pathohistological examination, were the same as those obtained on the mice to which the triglyceride of the fatty acid only containing 2% by weight of ethanol was administered.

Accordingly, since the LD$_{50}$ acute oral of 24R,25-(OH)$_2$-D$_3$ was larger than 100 mg/kg of the body weight of each mouse, and the same results were obtained by the administration of 24S,25-(OH)$_2$-D$_3$ in the same manner as above, it can be said that 24,25-(OH)$_2$-D$_3$ is quite safe.

The present invention will be explained more in detail while referring to the following examples in which 24R,25-(OH)$_2$-D$_3$ was used, the confirmation of the structure of the optical isomer due to 24 position having been carried out following "Tetrahedron Letters", No. 6, pages 2203 to 2206, 1975.

The present invention is explained in more detail in the following Examples; however, it should be recognized that the scope of the present invention is not restricted to these Examples.

EXAMPLE 1

Treatment of the model animal suffering from myodystrophia

After obtaining male C57BL/6J dy/dy mice (hereinafter referred to as the present animal) of 4 weeks after birth from Japan Clea Co. and confirming that they were suffered from myodystrophia, a solution of 24R,25-(OH)$_2$-D$_3$ prepared by dissolving thereof in an aqueous 0.001% solution of isopropyl alcohol (containing 24R,25-(OH)$_2$-D$_3$ corresponding to the daily rate of 0.1 μg/kg body weight or 1 μg/kg body weight) was given ad lib. to Groups I and II of the present animal as drinking water from the 5th week after birth. In addition, to the control group of the present aminal, an aqueous 0.001% solution of isopropyl alcohol was given ad lib. as drinking water. Further, to the untreated group of the present animal, tap water was given ad lib. as drinking water.

The rate of survival of the mice of each group after 150 days of giving the specified drinking water (150 days correspond to the average life of the present animal of 4 to 5 months shown in "Handbook for Model Animals of Diseases" Ed. by ISHIYAKU Publishing Co., page 421) as the result of tests in Example 1 is shown in Table 1 below.

TABLE 1

| Group | Dosage of the present substance per kg day | Drinking water | Rate of Survival (%) |
|---|---|---|---|
| Group I | 0.1 μg | aq. 0.001% isopropyl alcohol | 60 |
| Group II | 1.0 μg | aq. 0.001% | 100 |

TABLE 1-continued

| Group | Dosage of the present substance per kg day | Drinking water | Rate of Survival (%) |
|---|---|---|---|
| Control | — | isopropyl alcohol aq. 0.001% isopropyl alcohol | 16.7 |
| Not-treated | — | tap water | 16.7 |

The results shown in Table 1 demonstrate the effectiveness of the present substance of elongating the life of the patient animal.

EXAMPLE 2

Preparation of a pharmaceutical composition containing the present substance as an active ingredient Into one kilogram of triglyceride of $C_8$ to $C_{10}$ fatty acid, into which gaseous argon had been bubbled for 72 hours under irradiation from a 400 W high pressure mercury lamp, thereby having eliminated peroxides originally contained therein, 5 mg of 24R,25-$(OH)_2$-$D_3$ were dissolved. The thus obtained solution and a wall component prepared by combining the following components under heating were subjected to a machine for producing soft capsules to obtain the soft-encapsulated pharmaceutical composition containing one, two, five or 10 μg of 24R,25-$(OH)_2$-$D_3$ in one capsule was produced.

Recipe for soft capsule wall 10 parts by weight of gelatin,
2 parts by weight of glycerol,
0.05 part by weight of ethyl parahydroxybenzoate as an antiseptic,
0.2 part by weight of titanium white and
0.2 part by weight of water in the completed capsule.

What is claimed is:

1. A method for the treatment of myodystrophia, which comprises administering to a patient suffering from myodystrophia an effective amount of a compound of 24,25-dihydroxycholecalciferol.

2. A method according to claim 1, wherein said compound is 24R,25-dihydroxycholecalciferol.

* * * * *